(12) United States Patent
Tang et al.

(10) Patent No.: US 11,701,290 B2
(45) Date of Patent: Jul. 18, 2023

(54) MASSAGE HEAD FOR MASSAGE GUN AND MASSAGE GUN CONTAINING THE SAME

(71) Applicant: Zhejiang E-cozy Electronic Technology Co., Ltd., Zhejiang Province (CN)

(72) Inventors: Shousheng Tang, Zhejiang Province (CN); Daojin Tang, Zhejiang Province (CN)

(73) Assignee: Zhejiang E-cozy Electronic Technology Co., Ltd., Zhejiang Province (CN)

(*) Notice: Subject to any disclaimer, the term of this patent is extended or adjusted under 35 U.S.C. 154(b) by 410 days.

(21) Appl. No.: 17/027,326

(22) Filed: Sep. 21, 2020

(65) Prior Publication Data

US 2022/0040030 A1 Feb. 10, 2022

(51) Int. Cl.
*A61H 7/00* (2006.01)
*A61N 5/06* (2006.01)
(Continued)

(52) U.S. Cl.
CPC ............. *A61H 7/00* (2013.01); *A61N 5/0625* (2013.01); *A61H 23/00* (2013.01); *A61H 2201/0153* (2013.01); *A61H 2201/0207* (2013.01); *A61H 2201/0214* (2013.01); *A61H 2201/1654* (2013.01); *A61N 2005/005* (2013.01); *A61N 2005/063* (2013.01); *A61N 2005/0654* (2013.01)

(58) Field of Classification Search
CPC .. A61H 7/00; A61H 23/00; A61H 2201/0153; A61H 2201/0207; A61H 2201/1654; A61H 15/02; A61H 2201/0214; A61N 5/0625; A61N 2005/005; A61N 2005/063; A61N 2005/0654; A61N 2205/005
See application file for complete search history.

(56) References Cited

U.S. PATENT DOCUMENTS

| 10,182,642 B2* | 1/2019 | Khormaei ............... B05B 17/06 |
| 2005/0113725 A1* | 5/2005 | Masuda ............. A61H 23/0263 601/72 |

(Continued)

*Primary Examiner* — Philip R Wiest
*Assistant Examiner* — Tyler A Raubenstraw
(74) *Attorney, Agent, or Firm* — Bay State IP, LLC

(57) ABSTRACT

A massage head for a massage gun and a massage gun containing the same, relates to the technical field of massage devices, and solves the technical problem of the single function of the massage gun. The massage head comprises a massage head cover, a massage member, a cooling and heating component and a conductive quick-connecting component; wherein the massage head cover and the massage member are provided oppositely, the massage head cover and the massage member encircle an accommodating cavity for accommodating the cooling and heating component, and the conductive quick-connecting component is provided at the end of the massage head cover away from the massage member and electrically connected to the cooling and heating component; the massage head is detachably electrically connected to the massage gun body through the conductive quick-connecting component; the massage gun comprises a massage gun body, a grip handle, a reciprocating driving mechanism, a main circuit board, and a massage head.

7 Claims, 4 Drawing Sheets

(51) Int. Cl.
    *A61H 23/00*    (2006.01)
    *A61N 5/00*     (2006.01)

(56) References Cited

U.S. PATENT DOCUMENTS

| | | | |
|---|---|---|---|
| 2007/0027411 A1* | 2/2007 | Ella | A61H 9/005 601/7 |
| 2010/0137755 A1* | 6/2010 | Nagano | A61H 15/00 601/112 |
| 2010/0274162 A1* | 10/2010 | Evans | A61H 15/0092 601/46 |
| 2011/0009783 A1* | 1/2011 | Dverin | A61H 15/0085 606/33 |
| 2017/0172837 A1* | 6/2017 | Yang | A61H 23/0254 |
| 2017/0304145 A1* | 10/2017 | Pepe | A61H 23/02 |
| 2018/0280720 A1* | 10/2018 | Tatsumura Hillyer | A61N 5/0619 |
| 2020/0173629 A1* | 6/2020 | Li | F21L 4/085 |
| 2021/0128402 A1* | 5/2021 | Dai | A61H 23/0263 |

* cited by examiner

MASSAGE HEAD FOR MASSAGE GUN AND MASSAGE GUN CONTAINING THE SAME

CROSS REFERENCE TO RELATED APPLICATION

This application claims priority to Chinese Patent. Application No. 202010787720.2, filed Aug. 7, 2020, the contents of which are hereby incorporated by reference in their entirety.

TECHNICAL FIELD

The present invention relates to the technical field of massage devices, in particular to a massage head for a massage gun and a massage gun containing the same.

BACKGROUND

A massage gun is a structure of a massage device, such as a pistol, comprising a horizontal housing and a longitudinal handle. A massage head is provided at the front end of the housing, and a reciprocating driving device is provided in the housing. The massage head and the reciprocating driving device are connected by a mechanical structure to reciprocate and vibrate, and the massage head is pressed against the muscles to vibrate the muscles to achieve the effect of relaxing muscles and promoting blood circulation.

The applicant found that the prior an has at least the following technical problems.

The existing massage gun only has the massage physical therapy function and has no other functions. The reciprocating driving device is provided in the housing, and the power supply line can be routed in the housing. Therefore, the massage head and the reciprocating driving device in the housing should only be mechanically connected; however, this massage gun has a single function and a limited scope of application, and cannot meet the original higher demand for physical therapy of people.

SUMMARY

The object of the present invention is to provide a massage head for a massage gun and a massage gun containing the same to solve the technical problem of the single function of the massage gun in the prior art.

In order to achieve the above object, the present invention provides the following technical solutions.

The present invention provides a massage head for a massage gun, comprising a massage head cover, a massage member, a cooling and heating component and a conductive quick-connecting component, wherein:

the massage head cover is a horn-shaped structure;

the massage member is a cover-shaped structure;

the massage head cover and the massage member are provided oppositely, the massage head cover and the massage member encircle an accommodating cavity for accommodating the cooling and heating component, and the conductive quick-connecting component is provided at the end of the massage head cover away from the massage member and electrically connected to the cooling and heating component; and the massage head is detachably electrically connected to the massage gun body through the conductive quick-connecting component.

As a further improvement of the present invention, the conductive quick-connecting component comprises an aviation plug male connector provided on the massage head cover and an aviation plug female connector provided on the massage gun body.

As a further improvement of the present invention, the cooling and heating component comprises a temperature sensing element, a cooling and heating part, a heat-dissipating aluminum part, a heat-dissipating fan, a light-transmitting member and a cooling and heating circuit board provided in sequence, the temperature sensing element is provided on the inner wall of the massage member and is electrically connected to the cooling and heating circuit board; the cooling and heating part is provided close to or adhered to the massage member, the massage member is made of metal material; the cooling and heating part and the heat-dissipating fan are both connected with the cooling and heating circuit board cable; and the cooling and heating circuit board is electrically connected with the aviation plug male connector.

As a further improvement of the present invention, both the massage head cover and the light-transmitting member are provided with a plurality of sets of heat-dissipating holes communicated with the accommodating cavity.

As a further improvement of the present ion, the heat-dissipating aluminum part is a U-shaped structure and is provided with a groove for accommodating the cooling and heating part at the top, the depth of the groove is equivalent to the thickness of the cooling and heating part; the two side walls of the groove and the top wall of the U-shaped cavity of the heat-dissipating aluminum part are all fin-shaped structures; the heat-dissipating fan is provided in the U-shaped cavity of the heat-dissipating aluminum part, and the depth of the U-shaped cavity of the heat-dissipating aluminum part is smaller than the height of the heat-dissipating fan; the light-transmitting member is a cover-shaped structure with one side open and is sleeved on the top edge of the massage head cover, the cooling and heating circuit board is a ring-shaped structure and is sleeved on the outer side of the protrusion on the sealing side of the light-transmitting member; and a plurality of uprights are provided inside the light-transmitting member, which encircle a neck for clamping the heat-dissipating fan.

As a further improvement of the present invention, the protrusion is a hollow cylindrical structure and is communicated with the inner cavity of the light-transmitting member, when the aviation plug male connector is fixed on the end of the massaging head cover, its wiring terminal is located in the protrusion, and the cooling and heating circuit board is connected to the wiring terminal of the aviation plug male connector through a cable.

As a further improvement of the present invention, the cooling and heating circuit board is provided with light-emitting lamps, the bottom of the light-transmitting member is provided with an opening through which the light-emitting lamps pass, light-transmitting holes are provided with at the peripheral side of the light-transmitting member and at the position of the peripheral side of the massage head cover close to the light-emitting lamps.

As a further improvement of the present invention, a connecting column is provided on the massage member, an internal thread section is provided in the connecting column, light holes or threaded holes are provided at the corresponding position on the massage head cover, the light-transmitting member is provided with a through hole at the position corresponding to the connecting column, and the massage head cover is fixedly connected with the massage member by screws.

As a further improvement of the present invention, the light-transmitting member comprises a decorative ring provided on the top edge, and the outer diameter of the decorative ring is equal to the outer diameter of the massage head cover.

The present invention provides a massage gun, comprising a massage gun body, a grip handle connected with the massage gun body, a reciprocating driving mechanism and a main circuit board provided in the massage gun body, and the massage head to which the massage gun body is detachably connected;

wherein the aviation plug female connector of the conductive quick-connecting component is provided at the front end of the massage gun body and is in transmission connection with the reciprocating driving mechanism;

the aviation plug male connector of the conductive quick-connecting component is provided at the end of the massage head and is electrically connected to the cooling and heating component;

the aviation plug male connector is electrically connected to the main circuit board.

Compared with the prior art, the present invention has the following beneficial effects.

The massage head provided by the present invention not only has the function of vibration massage, but also can realize vibration massage while performing heat therapy or cold compress by providing a cooling and heating component inside the massage head, enriches the functions of the massage gun, and has a wider application range; by adopting a conductive quick-connecting component, the mechanical connection and electrical connection between the massage head and the massage gun body can be realized at the same time, which not only solves the wiring problem that an electrical component is provided inside the massage head, but also solves the problem that e massage head is connected to the massage gun body. The conductive quick-connecting component also simplifies the wiring structure, reduces wiring, and improves the life of the device.

BRIEF DESCRIPTION OF THE DRAWINGS

In order to explain the embodiments of the present invention or the technical solutions in the prior art more clearly, the drawings that need to be used in the description of the embodiments or the prior art will be briefly introduced hereinafter. Obviously, the drawings in the following description are only some embodiments of the present invention. For those skilled in the art, other drawings can be obtained based on these drawings without creative work.

In the figures, 1. Massage head cover; 11, Cylindrical part; 12. Flaring part; 13. Base; 2. Massage member; 3. Cooling and heating component; 31. Cooling and heating part; 32. Heat-dissipating aluminum part; 321. Groove; 33. Heat-dissipating fan; 34. Light-transmitting member; 341. Decorative ring; 342. Protrusion; 343. Opening; 35. Cooling and heating circuit board; 36. Light-emitting lamp; 37. Light-transmitting hole; 4. Conductive quick-connecting component; 41. Aviation plug male connector; 42. Aviation plug female connector; 5. Heat-dissipating hole; 100. Massage gun body; 200. Massage head; 300. Grip handle.

DESCRIPTION OF THE EMBODIMENTS

In order to make the objectives, technical solutions and advantages of the present invention clearer, the technical solutions of the present invention will be described in detail below. Obviously, the described embodiments are only some embodiments of the present invention, rather than all the embodiments. Based on the embodiments of the present invention, all other implementation manners obtained by those skilled in the art without creative work shall fall within the protection scope of the present invention.

Figure 1:
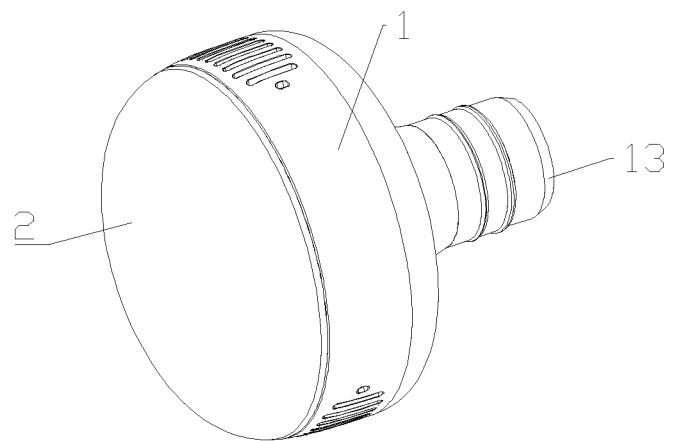
FIG. 1 is a schematic diagram of a three-dimensional structure of a massage head for a massage gun according to the present invention.

As shown in FIG. 1, the present invention provides a massage head for a massage gun, which comprises a massage head cover 1, a massage member 2, a cooling and heating component 3, and a conductive quick-connecting component 4, wherein:

the massage head cover 1 has a horn-shaped structure, comprising a cylindrical part 11, a flaring part 12 and a base 13, the base 13 is a hollow cylindrical structure, and the inner cavity is communicated with the inner cavities of the flaring part 12 and the cylindrical part 11;

the massage member 2 is a cover-shaped structure, and the massage member 2 is a part in contact with the human body, and in order to improve the comfort, the peripheral side of the massage member 2 is an arc transition structure:, the massage head cover 1 and the massage member 2 are provided oppositely, the massage head cover and the massage member encircle an accommodating cavity for accommodating he cooling and heating component 3, and the conductive quick-connecting component 4 is provided at the end of the massage head cover 1 away from the massage member 2, which is the base 13, and the conductive quick-connecting component 4 is electrically connected to the cooling and heating component 3; and the massage head 200 is detachably electrically connected to the massage gun body 100 through the conductive quick-connecting component 4. Through the above structural design, when the massage head 200 is connected to the massage gun body 100 through the conductive quick-connecting component 4, the assembly of the massage gun is realized, that is, the massage head 200 is connected to the massage gun body 100, and the electrical component in the massage gun body 100 can also supply power to the cooling and heating component 3.

Figure 3:
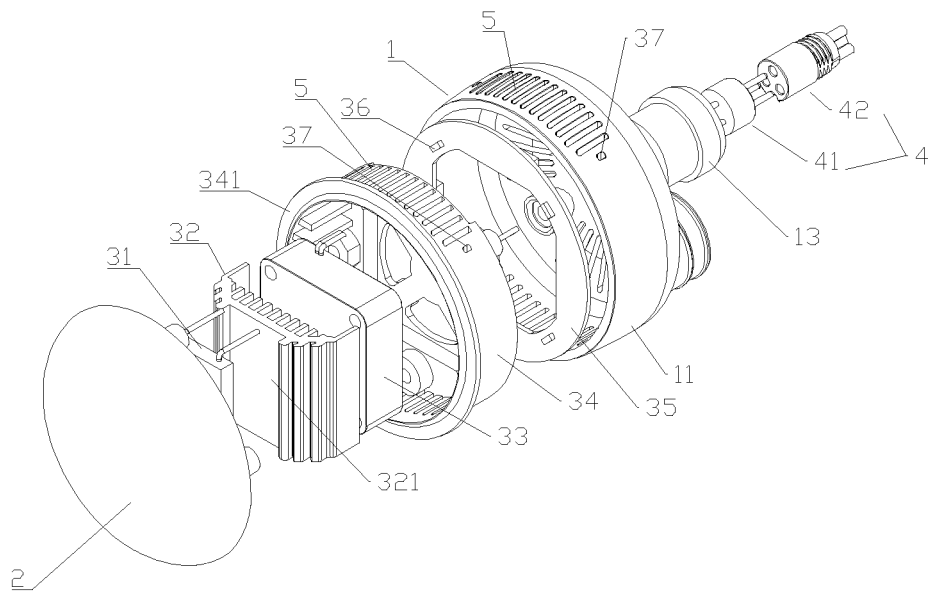
FIG. 3 is a first exploded diagram of a massage head for a massage gun according to the present invention.

As shown in FIG. 3, as an alternative embodiment of the present invention, the conductive quick-connecting component 4 comprises an aviation plug male connector 41 provided on the massage head cover 1 and an aviation plug female connector 42 provided on the massage gun body 100. Both the aviation plug male connector 41 and the aviation plug female connector 42 are realized by using products in the prior art.

Figure 4:
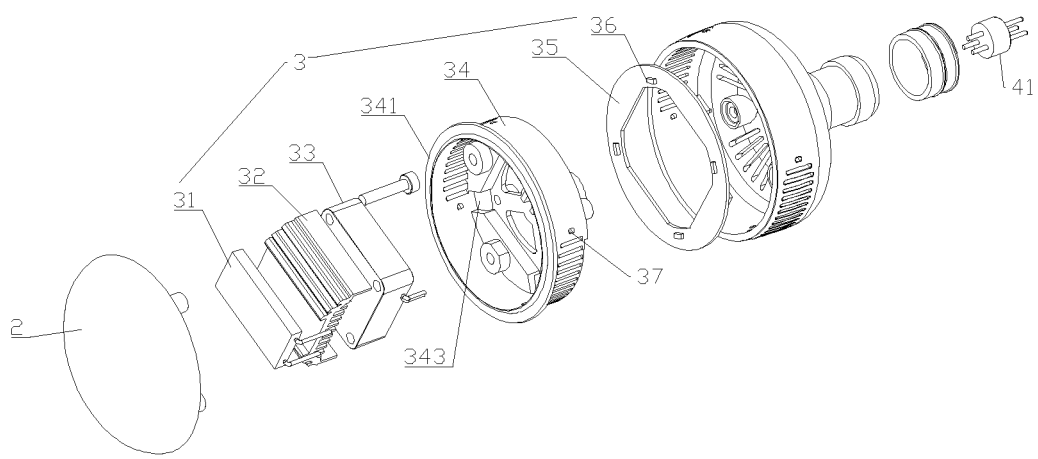
FIG. 4 is a second exploded diagram of a massage head for a massage gun according to the present invention.

As shown in FIG. 4, the cooling and heating component 3 comprises a temperature sensing element, a cooling and heating part 31, a heat-dissipating aluminum part 32, a heat-dissipating fan 33, a light-transmitting member 34 and a cooling and heating circuit board 35 provided in sequence. The temperature sensing element is provided on the inner wall of the massage member 2 and is electrically connected to the cooling and heating circuit board 35, so as to measure the temperature of the massage member 2, control the cooling and heating circuit board 35 through the main circuit board in the massage gun body 100, and finally adjust the cooling or heating capacity of the cooling and heating part 31 to increase or decrease the cooling or heating temperature and meet the needs of treatment; the cooling and heating part 31 is provided close to or adhered to the massage member 2, in order to improve the conduction of cooling capacity and heat and reduce energy loss. The massage member 2 is made of metal material to further improve the conduction efficiency and improve the effect of cold compress and heat therapy; the cooling and heating part 31 and the heat-dissipating fan 33 are both connected with the cable of the cooling and heating circuit board 35; and the cooling and heating circuit board 35 is electrically connected with the aviation plug male connector 41. It should be noted that the light-transmitting member 34 is made of a transparent material.

It should be noted that, in an alternative embodiment of the present invention, the temperature sensing element is an NTC thermistor.

In order to ensure a good heat-dissipating effect, both the massage head cover 1 and the light-transmitting member 34 are provided with a plurality of sets of heat-dissipating holes 5 communicated with the accommodating cavity.

Figure 5:
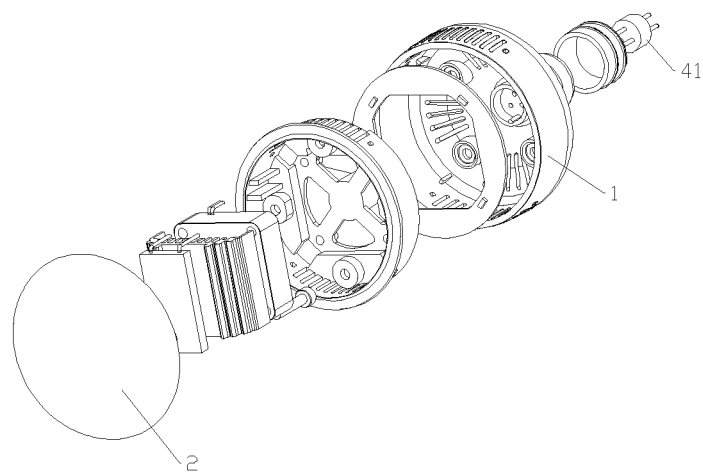
FIG. 5 is a third exploded diagram of a massage head for a massage gun according to the present invention.

As shown in FIGS. 3 and 5, the heat-dissipating aluminum part 32 is a U-shaped structure and is provided with a groove 321 for accommodating the cooling and heating part 31 at the top, the depth of the groove 321 is equivalent to the thickness of the cooling and heating part 31; the two side walls of the groove 321 and the top wall of the U-shaped cavity of the heat-dissipating aluminum part 32 are all fin-shaped structures. A fin-shaped structure is provided to improve the heat-dissipating effect, so as to improve the rapid export of heat emitted by the cooling and heating part 31 during cooling, increase the life of the cooling and heating part 31, and improve the cooling effect; the heat-dissipating fan 33 is provided in the U-shaped cavity of the heat-dissipating aluminum part 32, and the depth of the U-shaped cavity of the heat-dissipating aluminum part 32 is smaller than the height of the heat-dissipating fan 33; the light-transmitting member 34 is a cover-shaped structure with one side open, and the specification of the light-transmitting member 34 is compatible with the specification of the massage head cover 1; the light-transmitting member 34 is provided to facilitate fixing the cooling and heating circuit board 35 and fixing the heat-dissipating fan 33. The light-transmitting member 34 is sleeved on the top edge of the massage head cover 1. In order to reduce weight and simplify the structure, the sealing side of the light-transmitting member 34 is a hollow structure; the cooling and heating circuit hoard 35 is a ring-shaped structure and is sleeved on the outer side of the protrusion 342 on the sealing side of the light-transmitting member 34; and a plurality of uprights are provided inside the light-transmitting member 34, which encircle a neck for clamping the heat-dissipating fan 33.

Figure 6:
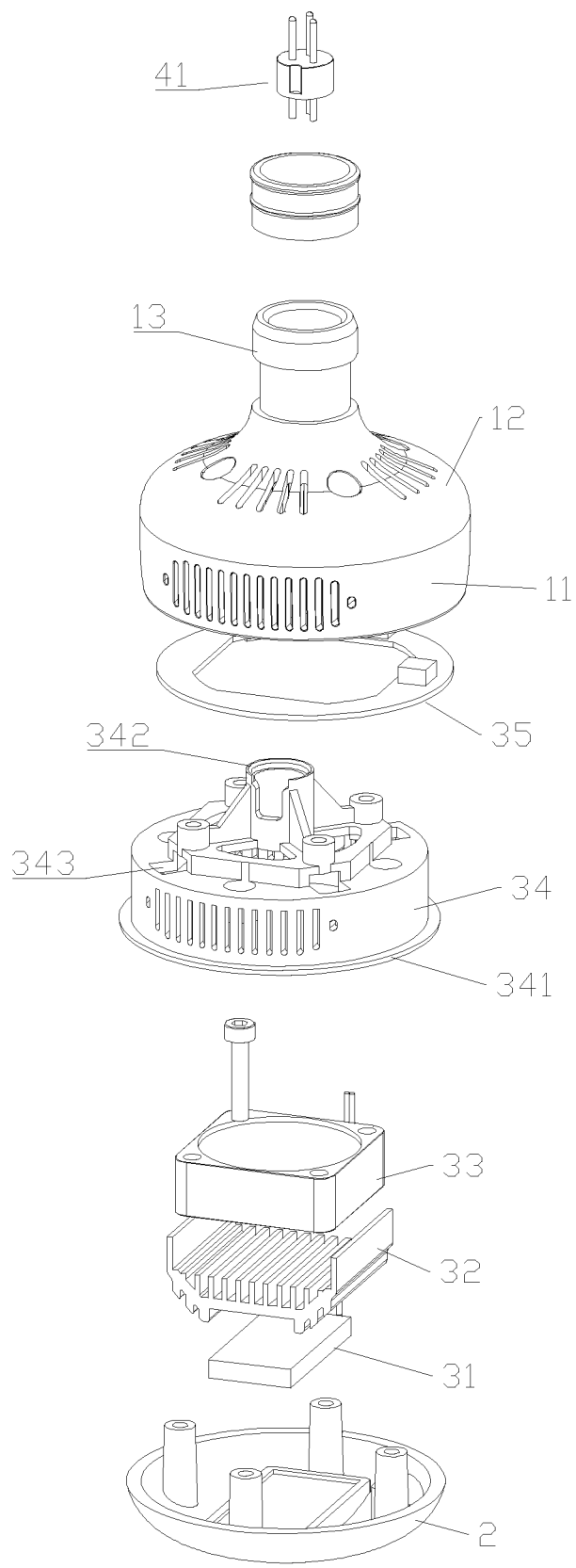
FIG. 6 is a fourth exploded diagram of a massage head for a massage gun according to the present invention.

As shown in FIG. 6, it should be noted that the protrusion 342 is a hollow cylindrical structure and is communicated with the inner cavity of the light-transmitting member 34, when the aviation plug male connector 41 is fixed on the end of the massaging head cover 1, its wiring terminal is located in the protrusion 342, and the cooling and heating circuit board 35 is connected to the wiring terminal of the aviation plug male connector 41 through a cable. Further, the aviation plug male connector 41 is connected to the base 13 by means of interference fit connection, screw connection, or the like.

The cooling and heating circuit board 35 is provided with light-emitting lamps 36, the bottom of the light-transmitting member 34 is provided with an opening 343 through which the light-emitting lamps 36 pass, light-transmitting holes 37 are provided with at the peripheral side of the light-transmitting member 34 and at the position of the peripheral side of the massage head cover 1 close to the light-emitting lamps 36. The light emitted by the light-emitting lamps 36 can be seen from the outside of the massage head cover 1 through the light-transmitting holes 37. There may a plurality of light-emitting lamps 36, and the light of different colors can be emitted according to different working functions of the massage gun to facilitate the judgment of the user. The light-transmitting member 34 is made of transparent material, the light of different colors emitted by the light-emitting lamps 36 can also be displayed through the decorative ring of the light-transmitting member 34, which is not only more beautiful, but also convenient to identify the function of the massage gun.

A connecting column is provided on the massage member 2, an internal thread section is provided in the connecting column, light holes or threaded holes are provided at the corresponding position on the massage head cover 1, the light-transmitting member 34 is provided with a through hole at the position corresponding to the connecting column, and the massage head cover 1 is detachably fixedly connected with the massage member 2 by screws.

The light-transmitting member 34 comprises a decorative ring 341 provided on the top edge, and the outer diameter of the decorative ring 341 is equal to the outer diameter of the massage head cover 1. When the massage member 2 and the massage head cover 1 are connected together, the decorative ring 341 becomes a ring-shaped decorative structure. Since the decorative ring 341 is made of transparent material, the colored light emitted by the light-emitting lamps 36 will make the decorative ring 341 show a colorful effect.

Figure 2:
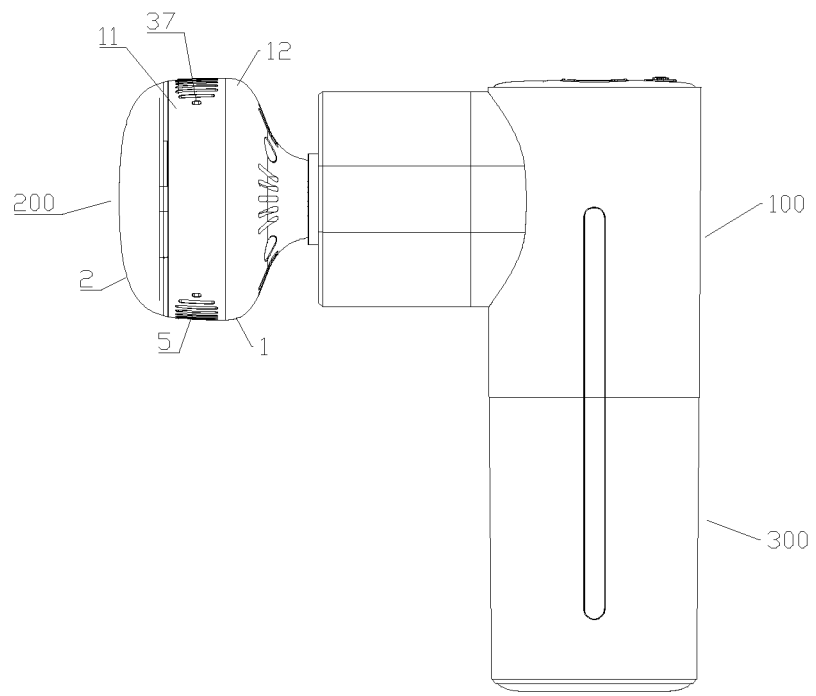
FIG. 2 is a front diagram of a massage gun according to the present invention.

As shown in FIG. 2, the present invention provides a massage gun, comprising a massage gun body 100, a grip handle 300 connected with the massage gun body 100, a reciprocating driving mechanism and a main circuit board provided in the massage gun body 100, and the massage head 200 to which the massage gun body 100 is detachably connected;

wherein the aviation plug female connector 42 of the conductive quick-connecting component 4 is provided at the front end of the massage gun body 100 and is in transmission connection with the reciprocating driving mechanism;

the aviation plug male connector 41 of the conductive quick-connecting component 4 is provided at the end of the massage head 200 and is electrically connected to the cooling and heating component 3;

the aviation plug male connector 2 is electrically connected to the main circuit board.

The massage head provided by the present invention not only has the function of vibration massage, but also can realize vibration massage while performing heat therapy or cold compress by providing a cooling and heating component inside the massage head, enriches the functions of the massage gun, and has a wider application range; by adopting a conductive quick-connecting component, the mechanical connection and electrical connection between the massage head and the massage gun body can be realized at the same time, which not only solves the wiring problem that an electrical component is provided inside the massage head, but also solves the problem that the massage head is connected to the massage gun body. The conductive quick-connecting component also simplifies the wiring structure, reduces wiring, and improves the life of the device.

It should be first noted here that "inward" refers to the direction toward the center of the accommodating space, and "outward" refers to the direction away from the center of the accommodating space.

In the description of the present invention, it should be understood that the terms indicating the orientation or the positional relationship, such as "center", "longitudinal", "transverse", "length", "width", "thickness", "upper", "lower", "front", "back", "left", "right", "vertical", "horizontal", top", "bottom","inner", "outer", "clockwise", "counterclockwise", "axial", "radial", "circumferential", etc., are based on the orientation or the positional relationship shown in FIG. 1, and are only for the convenience of describing the present invention and simplifying the description, rather than indicating or implying that the indicated device or element must have a specific orientation, be constructed and operated in a specific orientation, and therefore cannot be understood as a limitation of the present invention.

In addition, the terms "first" and "second" are only used for descriptive purposes, and cannot be understood as indicating or implying relative importance or implicitly indicating the number of indicated technical features. Therefore, the features defined with "first" and "second" may explicitly or implicitly include at least one of the features. In the description of the present invention, "a plurality of" means at least two, such as two, three, etc., unless otherwise specifically defined.

In the present invention, unless otherwise clearly defined and limited, the terms "install", "link", "connect", "fix" and the like should be understood in a broad sense, for example, it may be a fixed connection or a detachable connection, or may be integrated; it may be a mechanical connection, or may be an electrical connection; it may be a direct connection, or an indirect connection through an intermediate medium, and it may be the internal communication of two elements or the interaction relationship between two elements, unless otherwise specifically defined. For those skilled in the art, the specific meanings of the above terms in the present invention can be understood according to specific circumstances.

In the present invention, unless otherwise clearly stated and defined, the first feature "on" or "under" the second feature may include the first feature and the second feature in direct contact with each other, or may include the first feature and the second feature in indirect contact with each other through an intermediary. Moreover, the first feature "above", "on" and "over" the second feature may include the first feature directly above and obliquely above the second feature, or simply means that the first feature is higher in level than the second feature. The first feature "below", "under" and "underneath" the second feature may include the first feature directly below and obliquely below the second feature, or simply means that the first feature is lower in level than the second feature.

In the description of this specification, descriptions with reference to the terms "one embodiment", "some embodiments", "examples", "specific examples", or "some examples" etc. mean that specific features, structures, materials or characteristics described in conjunction with the embodiment or example are included in at least one embodiment or example of the present invention. In this specification, the schematic representations of the above terms do not necessarily refer to the same embodiment or example. Moreover, the described specific features, structures, materials, or characteristics can be combined in any one or more embodiments or examples in an appropriate manner. In addition, those skilled in the art can integrate and combine the different embodiments or examples and the features of the different embodiments or examples described in this specification without contradicting each other.

The above are only specific embodiments of the present invention, but the protection scope of the present invention is not limited thereto. Any changes or substitutions conceivable to those skilled in the art within the technical scope disclosed by the present invention should be covered within the protection scope of the present invention. Therefore, the protection scope of the present invention should be subject to the protection scope of the claims.

What is claimed is:

1. A massage head for a massage gun, comprising a massage head cover, a massage member, a cooling and heating component and a conductive quick-connecting component, wherein:

the massage head cover is a horn-shaped structure;

the massage member is a cover-shaped structure;

the massage head cover and the massage member are provided oppositely, the massage head cover and the massage member encircle an accommodating cavity for accommodating the cooling and heating component, and the conductive quick-connecting component is provided at the end of the massage head cover away from the massage member and electrically connected to the cooling and heating component; and the massage head is detachably electrically connected to the massage gun body through the conductive quick-connecting component;

wherein the cooling and heating component comprises a temperature sensing element, a cooling and heating part, a heat-dissipating aluminum part, a heat-dissipating fan, a light-transmitting member and a cooling and heating circuit board provided in sequence, the temperature sensing element is provided on the inner wall of the massage member and is electrically connected to the cooling and heating circuit board; the cooling and heating part is provided close to or adhered to the massage member, the massage member is made of metal material; the cooling and heating part and the heat-dissipating fan are both connected with the cooling and heating circuit board cable; and the cooling and heating circuit board is electrically connected with the aviation plug male connector; and wherein the heat-dissipating aluminum part is a U-shaped structure and is provided with a groove for accommodating the cooling and heating part at the top, the depth of the groove is equivalent to the thickness of the cooling and heating part; the two side walls of the groove and the top wall of the U-shaped cavity of the heat-dissipating aluminum part are all fin-shaped structures; the heat-dissipating fan is provided in the U-shaped cavity of the heat-dissipating aluminum part, and the depth of the U-shaped cavity of the heat-dissipating aluminum part is smaller than the height of the heat-dissipating fan; the light-transmitting member is a cover-shaped structure with one side open and is sleeved on the top edge of the massage head cover, the cooling and heating circuit board is a ring-shaped structure and is sleeved on the outer side of the protrusion on the sealing side of the light-transmitting member; and a plurality of uprights are provided inside the light-transmitting member, which encircle a neck for clamping the heat-dissipating fan.

2. The massage head for a massage gun according to claim 1, wherein the conductive quick-connecting component comprises an aviation plug male connector provided on the massage head cover and an aviation plug female connector provided on the massage gun body.

3. The massage head for a massage gun according to claim 1, wherein both the massage head cover and the light-transmitting member are provided with a plurality of sets of heat-dissipating holes communicated with the accommodating cavity.

4. The massage head for a massage gun according to claim 1, wherein the protrusion is a hollow cylindrical structure and is communicated with the inner cavity of the light-transmitting member, when the aviation plug male connector is fixed on the end of the massaging head cover, its wiring terminal is located in the protrusion, and the cooling and heating circuit board is connected to the wiring terminal of the aviation plug male connector through a cable.

5. The massage head for a massage gun according to claim 1, wherein the cooling and heating circuit board is provided with light-emitting lamps, the bottom of the light-transmitting member is provided with an opening through which the light-emitting lamps pass, light-transmitting holes are provided with at the peripheral side of the light-transmitting member and at the position of the peripheral side of the massage head cover close to the light-emitting lamps.

6. The massage head for a massage gun according to claim 1, wherein the light-transmitting member comprises a decorative ring provided on the top edge, and the outer diameter of the decorative ring is equal to the outer diameter of the massage head cover.

7. A massage gun, comprising a massage gun body, a grip handle connected with the massage gun body, a reciprocating driving mechanism and a main circuit board provided in the massage gun body, and a massage head according to claim 1 to which the massage gun body is detachably connected;
    wherein the aviation plug female connector of the conductive quick-connecting component is provided at the front end of the massage gun body and is in transmission connection with the reciprocating driving mechanism;
    the aviation plug male connector of the conductive quick-connecting component is provided at the end of the massage head and is electrically connected to the cooling and heating component;
    the aviation plug male connector is electrically connected to the main circuit board.

\* \* \* \* \*